United States Patent
Patel et al.

(10) Patent No.: US 9,747,433 B2
(45) Date of Patent: Aug. 29, 2017

(54) WEARABLE ELECTRONIC DEVICE AND METHOD FOR SECURING SAME

(71) Applicant: MOTOROLA MOBILITY LLC, Chicago, IL (US)

(72) Inventors: Mitul R. Patel, Lake Zurich, IL (US); Sajid I Dalvi, Aurora, IL (US); Francis X. Kuzhiyil, Deerfield, IL (US); Eric V. Tashakkor, Des Plaines, IL (US)

(73) Assignee: Google Technology Holdings, LLC, Mountain View, CA (US)

( * ) Notice: Subject to any disclaimer, the term of this patent is extended or adjusted under 35 U.S.C. 154(b) by 0 days.

(21) Appl. No.: 14/464,837

(22) Filed: Aug. 21, 2014

(65) Prior Publication Data
US 2015/0371028 A1    Dec. 24, 2015

Related U.S. Application Data

(60) Provisional application No. 62/016,375, filed on Jun. 24, 2014.

(51) Int. Cl.
*G06F 7/04* (2006.01)
*G06F 21/44* (2013.01)
(Continued)

(52) U.S. Cl.
CPC ............ *G06F 21/44* (2013.01); *A61B 5/0002* (2013.01); *A61B 5/681* (2013.01); *A61B 5/6898* (2013.01);
(Continued)

(58) Field of Classification Search
CPC .................................. G06F 21/31; G06F 21/44
(Continued)

(56) References Cited

U.S. PATENT DOCUMENTS

2003/0025603 A1    2/2003  Smith
2004/0064728 A1    4/2004  Scheurich
(Continued)

FOREIGN PATENT DOCUMENTS

EP        2378748 A1    10/2011
WO   2015051253 A2     4/2015

OTHER PUBLICATIONS

Radovan Stojanovic & Dejan Karadaglic, "Design of Oximeter Based on LED-LED Configuration and FPGA Technology", Sensor 2013, 13, pp. 574-865.*

(Continued)

*Primary Examiner* — Luu Pham
*Assistant Examiner* — Canh Le
(74) *Attorney, Agent, or Firm* — Shumaker & Sieffert, P.A.

(57) ABSTRACT

The disclosure is directed to a wearable device that is configured to secure itself based on signals received from a pulse sensor. According to one implementation, the pulse sensor includes a light source (e.g., a light-emitting diode) and a photo sensor. The light source, under the control of a processor, shines light having a particular wavelength (e.g., green or infrared). The photo sensor generates signals based on light that it senses. For example, when the light from the light source reflects off a person's skin, then the photo sensor will generate signals based on the reflected light that the photo sensor detects. In this manner, the wearable device can accurately determine whether it is being worn by a user (e.g., by taking a photoplethysmogram) and, when necessary, secure the wearable electronic device.

8 Claims, 7 Drawing Sheets

(51) Int. Cl.
  *A61B 5/00* (2006.01)
  *G06F 21/32* (2013.01)
  *G06F 21/34* (2013.01)
  *H04L 29/06* (2006.01)
  *H04W 12/06* (2009.01)
  *G06F 21/35* (2013.01)

(52) U.S. Cl.
  CPC .............. *G06F 21/32* (2013.01); *G06F 21/34* (2013.01); *H04L 63/0853* (2013.01); *H04L 63/0861* (2013.01); *H04W 12/06* (2013.01); *G06F 21/35* (2013.01)

(58) Field of Classification Search
  USPC .......................................................... 726/16
  See application file for complete search history.

(56) References Cited

U.S. PATENT DOCUMENTS

| | | | |
|---|---|---|---|
| 2008/0235144 A1 | 9/2008 | Phillips | |
| 2014/0062892 A1* | 3/2014 | Dickinson et al. | 345/173 |
| 2014/0073486 A1 | 3/2014 | Ahmed et al. | |
| 2014/0085050 A1 | 3/2014 | Luna | |
| 2014/0135631 A1* | 5/2014 | Brumback et al. | 600/479 |
| 2014/0139637 A1* | 5/2014 | Mistry et al. | 348/46 |
| 2014/0213863 A1* | 7/2014 | Loseu et al. | 600/324 |
| 2014/0275852 A1* | 9/2014 | Hong et al. | 600/301 |
| 2015/0039880 A1* | 2/2015 | Aminzade | 713/100 |
| 2015/0145673 A1* | 5/2015 | Choi et al. | 340/539.12 |

OTHER PUBLICATIONS

Igor Crk and Chris Gniady, "Understanding Energy Consumption of Sensor Enabled Applications on Mobile phones," 31 st Annual International Conference of the IEEE EMBS Minneapolis, Minnesota, USA, Sep. 2-6, 2009, pp. 6885-6888.*

Hyonyoung Han et al. "Development of real-time motion artifact reduction algorithm for a wearable photoplethysmorgraphy," Proceedings of the 29th Annual International Conferencxe of the IEEE EMBS Cite Internationale, Lyon, France Aug. 23-26, 2007, pp. 1538-1541.*

International Search Report and Written Opinion of International Application No. PCT/US2015/037279, mailed Oct. 8, 2015, 13 pp.

Ritchie, "Apple Watch, Apple Pay, and wrist detection: What you need to know," retrieved from URL:http://www.imore.com/apple-watch-apple-pay-and-wrist-detection-what-you-need-know, Sep. 30, 2015, 14 pp.

International Preliminary Report on Patentability from International Application No. PCT/US2015/037279, mailed Jan. 5, 2017,9 pp.

* cited by examiner

WEARABLE ELECTRONIC DEVICE AND METHOD FOR SECURING SAME

CROSS-REFERENCE TO RELATED APPLICATIONS

The present application claims priority to U.S. Provisional Patent Application 62/016,375, filed Jun. 24, 2014, the contents of which are incorporated herein by reference.

TECHNICAL FIELD

The present disclosure is related generally to wearable electronic devices and, more particularly, to a method and apparatus for securing a wearable electronic device.

BACKGROUND

Wearable electronic devices, such as smart watches, are becoming more popular. Such devices are able to synchronize with non-wearable devices, such as smart phones. For example, when a user receives a text message on a smart phone, the smart phone can push the message out to the wearable device. The wearable device may then display the message on a user interface (e.g., on a watch face).

One issue with wearable electronic devices is security. For example, when a person takes off his or her smart watch and leaves it on a table in a restaurant, a passerby may be able to see the user's email.

DRAWINGS

While the appended claims set forth the features of the present techniques with particularity, these techniques, together with their objects and advantages, may be best understood from the following detailed description taken in conjunction with the accompanying drawings of which:

DESCRIPTION

Figure 1A:
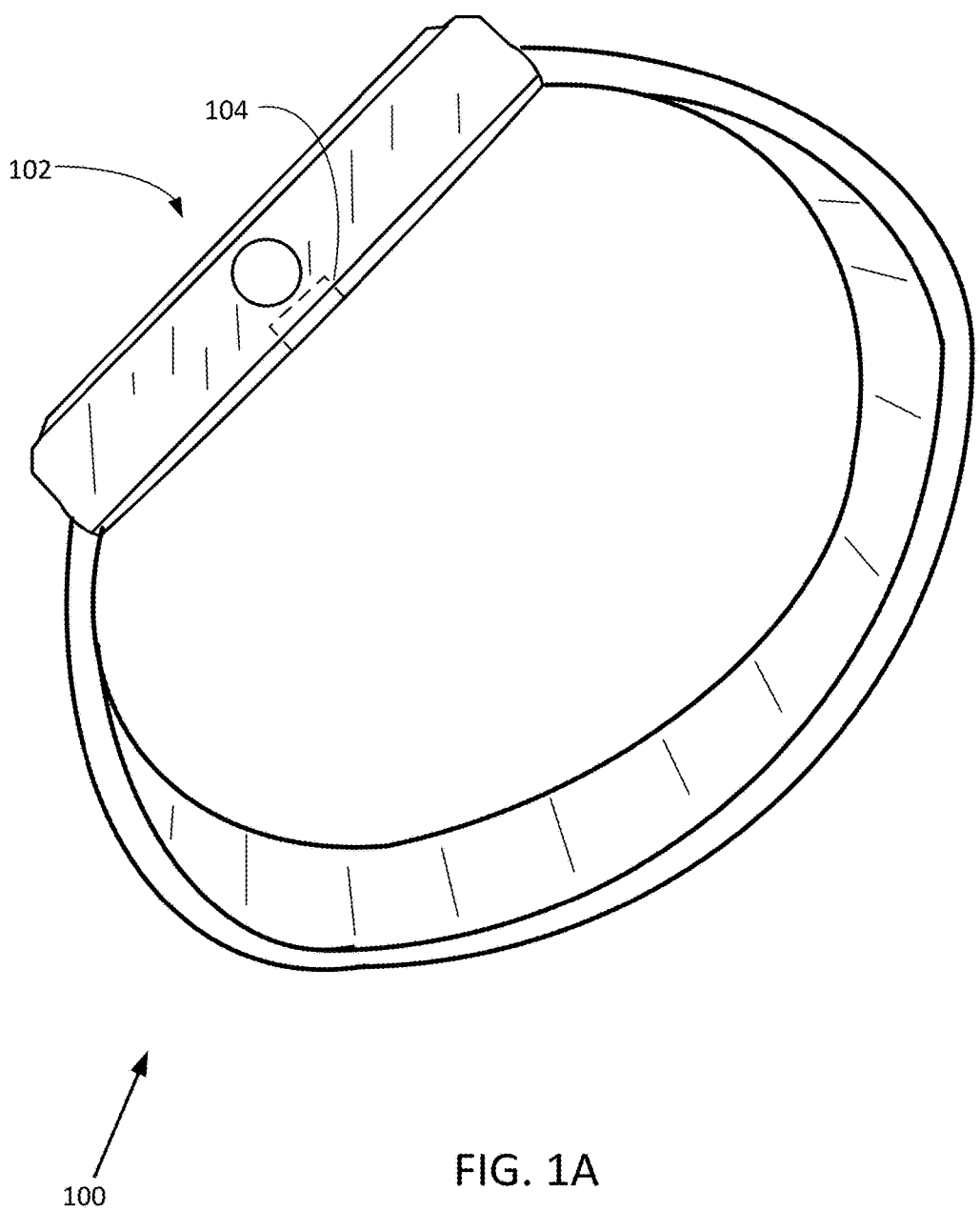
FIG. 1A is an exterior view of a wearable electronic device according to an embodiment.

This disclosure is generally directed to a method for securing a wearable electronic device ("wearable device"). According to various embodiments, the wearable device (e.g., a smart watch) determines whether a user's pulse is present. If the user's pulse is determined not to be present, the wearable device secures itself. For example, the wearable device may lock its user interface and prompt the user for the entry of a password or personal identification number. The wearable device may also signal another electronic device (e.g., a paired communication device, such as a smart phone) to indicate that the wearable device is no longer being worn by a user. The other electronic device (referred to herein as a "companion device") may then react by, for example, ceasing to push user messages (e.g., text messages or emails) wirelessly to the wearable device. The companion device may also react to the signal from the wearable device by prompting for entry of a password or personal identification number.

The disclosure is also directed to a wearable device that is configured to secure itself based on signals received from a pulse sensor. In an embodiment, the pulse sensor includes a light source (e.g., a light-emitting diode) and a photo sensor. The light source, under the control of a processor, shines light having a particular wavelength (e.g., green or infrared). The photo sensor generates signals based on light that it senses. For example, when the light from the light source reflects off a person's skin, then the photo sensor will generate signals based on the reflected light that the photo sensor detects. In one embodiment, the pulse sensor captures a photoplethysmogram ("PPG"), in which the reflected light from a person's skin creates a particular signature that the processor interprets to determine the presence of a pulse. In this manner, the wearable device can accurately determine whether it is being worn by a user. For example, when the wearable device is a smart watch, then the presence of a human pulse from the user's wrist will manifest in the reflected light signature and lead the processor to conclude that the watch is, in fact, being worn. This allows for greater certainty than, for example, using proximity detection alone, which may be triggered by mere proximity of an object, such as the surface of a table.

In an embodiment, the wearable device also has a proximity sensor, which may use the same components as the pulse sensor (e.g., the same light source and the same photo sensor). In some implementations, the power consumption required by the light source to perform PPG is greater than the power consumption the light source requires when performing proximity sensing. To address this issue, the wearable device may carry out a first pulse detection to verify that the wearable device is being worn (e.g., using the required power from the light source), and then carry out periodic proximity detections (e.g., by flashing the light source at a lower power periodically and sensing the reflection) to determine whether the user's skin is still present (i.e., proximal to the wearable device). If the wearable device does not detect the user's skin to be present, then the wearable device carries out a second pulse detection. The wearable device may then secure itself (or not) based on this second pulse detection.

In still another embodiment, the wearable device triggers its pulse check off of motion (e.g., as detected by a motion sensor). If, for example, the wearable device detects motion, then it checks for a pulse. If the wearable device detects a pulse, then it initiates an authentication procedure in which it prompts the user for a password or personal identification number (either directly through the user interface of the wearable device or via the companion device). If, however, the wearable device has previously gone through this procedure (e.g., the wearable device is already being worn, but the user just moves in a way that causes the wearable device to move), then the wearable device checks for a pulse. If the wearable device does not detect a pulse, the wearable device secures itself. If the wearable device does detect a pulse, then it leaves itself unsecured.

Figure 1B:
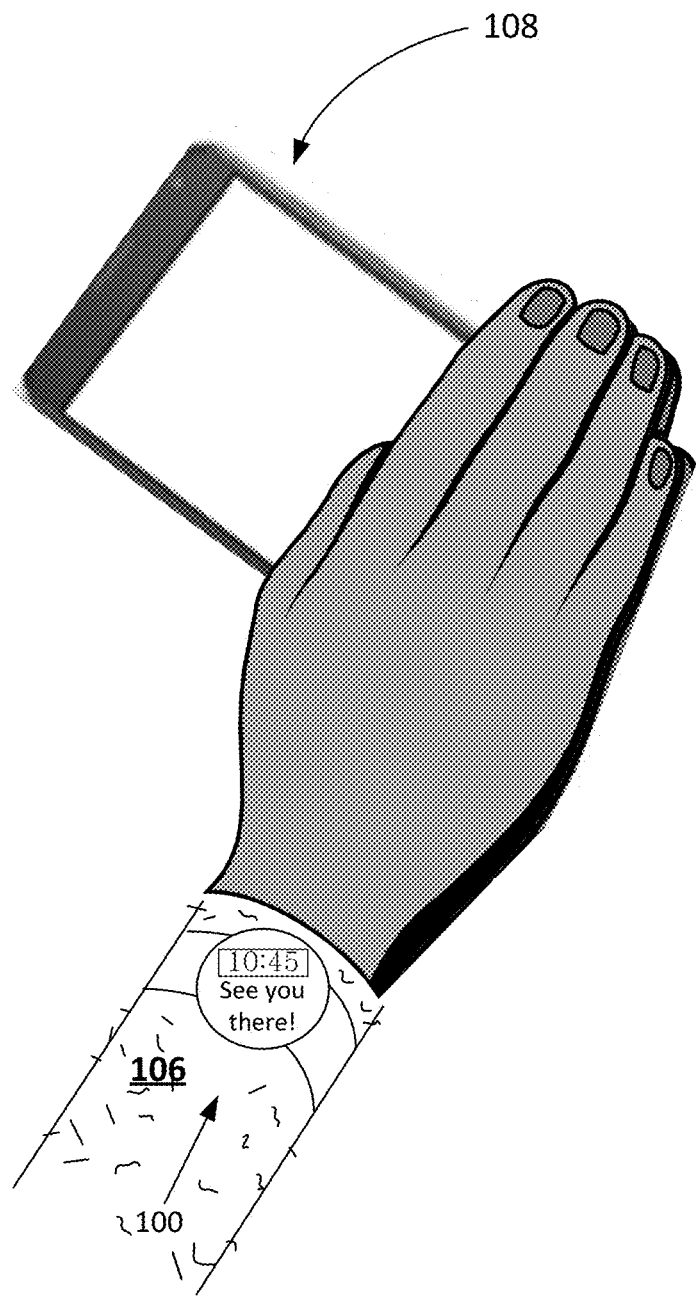
FIG. 1B is an exterior view of a wearable electronic device while it is being worn by a user, who is holding a companion electronic device.

Turning to FIG. 1A, a wearable electronic device 100 according to an embodiment includes a housing 102. The housing 102 may take a variety of forms, including a ring, wrist device (e.g., a wristwatch), and a pair of glasses. Within the housing 102 is a pulse sensor 104 (shown with phantom lines). The wearable electronic device 100 according to an embodiment is worn such that the pulse sensor 104 is proximate to a user's skin 106 (shown in FIG. 1B). In some embodiments, the wearable device 100 is paired with a companion device 108. Although shown in FIG. 1B as a smartphone, the companion device 108 may be implemented in a variety of ways, including a tablet computer or a notebook computer.

Figure 2:
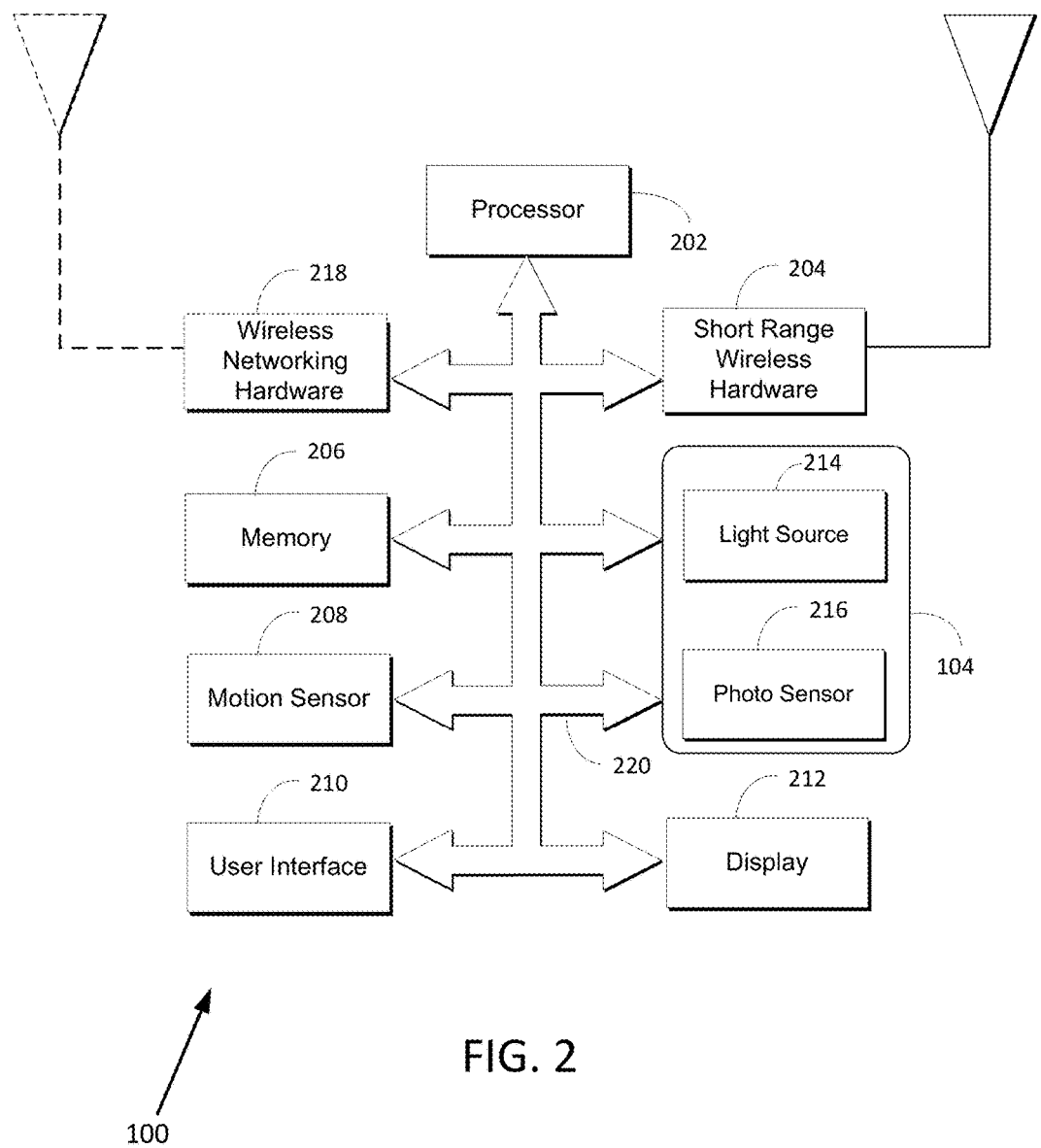
FIG. 2 is a block diagram depicting components of a wearable electronic device according to an embodiment.

Turning to FIG. 2, the wearable device 100 in an embodiment includes a processor 202. Several components are communicatively linked to the processor 202, including short-range wireless hardware 204 (e.g., a Bluetooth® chipset or a near-field communication chip), a memory 206, a motion sensor 208 (e.g., an accelerometer), a user interface 210 (e.g., a touch screen, buttons, or knobs), and a display 212 (e.g., an organic light emitting diode watch face). In some embodiments, the display 212 and the user interface 210 are the same physical component. The pulse sensor 104 includes a light source 214 (e.g., a light-emitting diode) and a photo sensor 216. The light source 214 is configured so that it shines light in a direction of a user. In this way, when the wearable device 100 is worn by a user, the light reflects off of the user's skin and is sensed by the photo sensor 216. In some embodiments, the pulse sensor 104 also functions as a proximity sensor. The memory 206 may be volatile, non-volatile, or a combination thereof. In some embodiments, the wearable device 100 also includes wireless networking hardware 218 (e.g., a WiFi chipset or a cellular baseband chipset), through which the wearable device 100 communicates with other devices over networks such as WiFi networks or cellular networks.

The elements of FIG. 2 are communicatively linked to one another via one or more data pathways 220. Possible implementations of the data pathways 220 include wires and conductive pathways on a microchip. Possible implementations of the processor 202 include a microprocessor and a controller.

Figure 3:
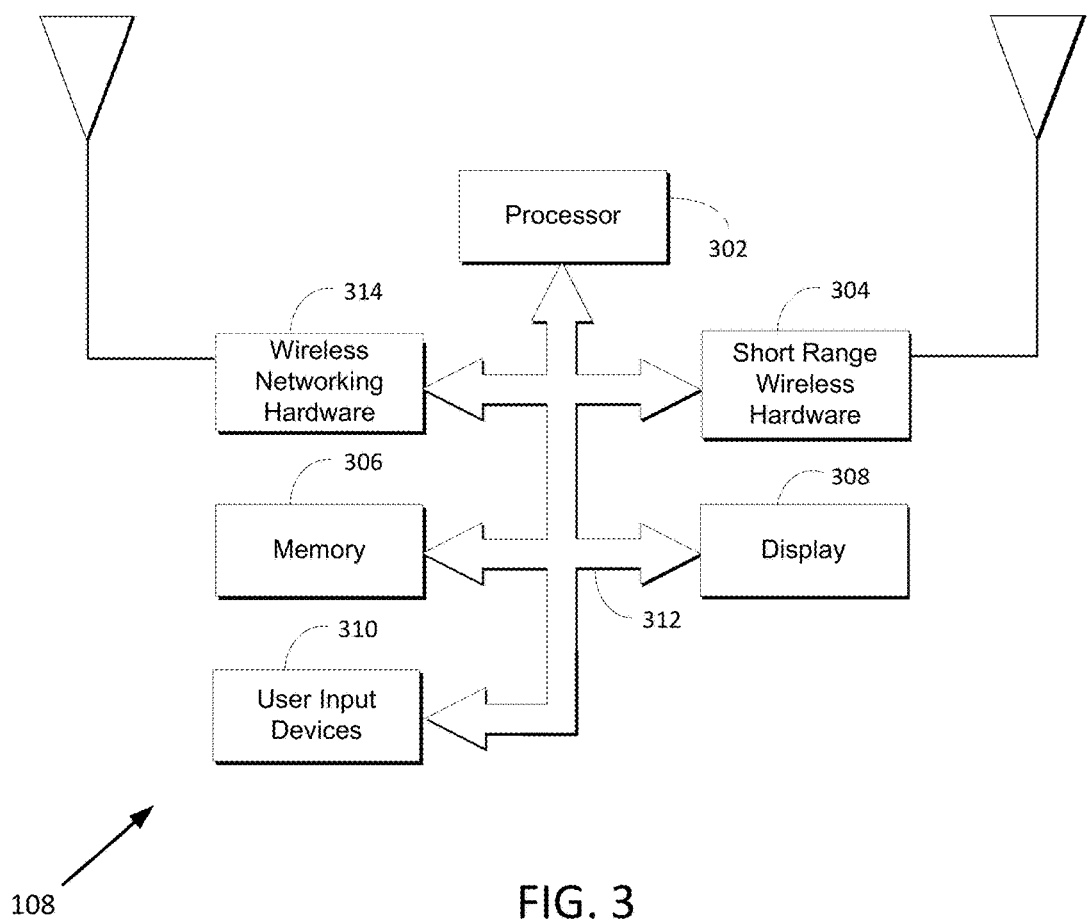
FIG. 3 is a block diagram depicting components of a companion electronic device according to an embodiment.

Turning to FIG. 3, the companion device 108 in an embodiment includes a processor 302. Several components are communicatively linked to the processor 302, including short-range wireless hardware 304 (e.g., a Bluetooth® chip set or a near-field communication chip), a memory 306, a display 308, and user input devices 310 (e.g., a capacitive touch screen, microphones, and physical buttons). The processor 302 transmits data to and receives data from the wearable device 100 via the short range wireless hardware 304. In some embodiments, the companion device 108 includes wireless networking hardware 314. In those embodiments, the processor 302 sends data to and receives data from other devices via a wireless local area network or a cellular network using the wireless networking hardware 314. The elements of FIG. 3 are communicatively linked to one another via one or more data pathways 312. Possible implementations of the data pathways 312 include wires and conductive pathways on a microchip. Possible implementations of the processor 302 include a microprocessor and a controller. The memory 306 may be volatile, non-volatile, or a combination thereof.

Figure 4:
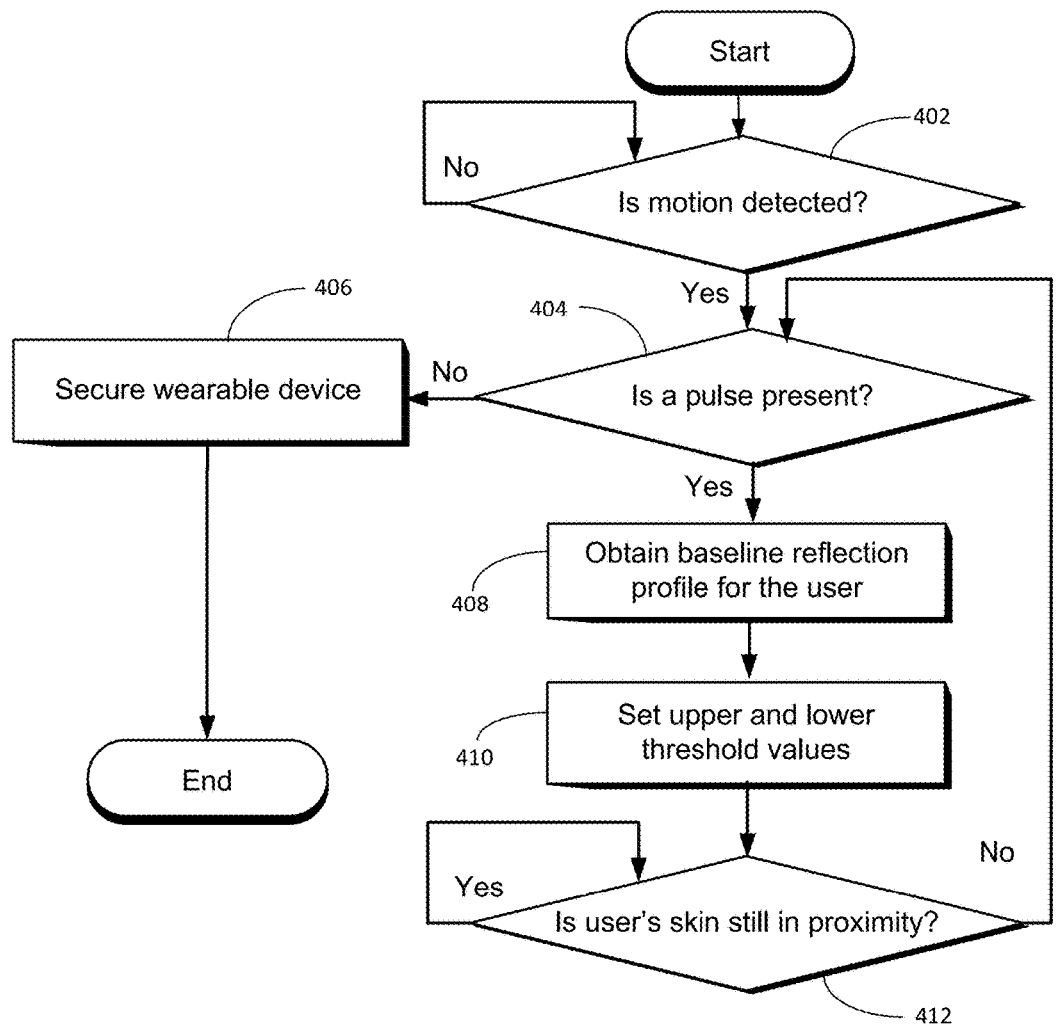
FIGS. 4, 5 and 6 show flowcharts that illustrate the operation of different embodiments.

Turning to FIG. 4, operation of the wearable device 100 according to an embodiment is described. In this embodiment, assume that the wearable device 100 is being worn by anyone and is at rest. At block 402, the wearable device 100 checks for motion (e.g., the processor 202 polls the motion sensor 208). If the wearable device 100 does not detect motion, then the process loops back to block 402. If the wearable device 100 detects motion (e.g., the user moves the wearable device 100 to check the time or the user takes the wearable device off), then the process moves to block 404, at which the wearable device 100 determines whether a pulse is present. For example, the processor 202 turns on the light source 214. The light from the light source reflects off of the user's skin 106. The reflected light is detected by the photo sensor 216. The photo sensor 216 then generates a signal based on the reflected light. The processor 202 reads the signal and determines, based on the signal, whether there is a pulse present (e.g., by using PPG). If the processor 202 determines that there is no pulse present, then the process moves to block 406, at which the processor 202 secures the wearable device 100 (e.g., by ceasing to display texts on the wearable device 100 or by signaling the companion device 108, which reacts by ceasing to send texts to the wearable device 100).

If, at block 404, the wearable device 100 determines that there is a pulse present, the wearable device 100 obtains a baseline reflection profile for the user at block 408. For example, the processor 202 turns on the light source 214. The light from the light source reflects off of the user's skin 106. The reflected light is detected by the photo sensor 216. The photo sensor 216 then generates a signal based on the reflected light. The processor 202 reads the signal and determines, based on the signal, what the user's skin reflection profile is (e.g., the wavelength at which light from the light source 214 reflects off of the user's skin 106). The skin reflection profile may depend on the user's skin tone and vary from user to user. At block 410, the wearable device 100 sets upper and lower threshold values for the user's skin reflection profile. For example, the processor, based on the user's skin profile, sets upper and lower threshold values for the wavelength (or upper and lower threshold values for the frequency) of the reflected light. At block 412, the wearable device 100 intermittently checks to see whether the user's skin 106 is still in proximity to the wearable device 100. For example, the wearable device flashes the light source 214 intermittently (e.g., every 5 milliseconds). The light from the light source 214 reflects off of the user's skin 106. The reflected light is detected by the photo sensor 216. The photo sensor 216 then generates a signal based on the reflected light. The processor 202 determines whether the wavelength or frequency of the reflected light is within upper and lower thresholds. If so, then the process continues to loop back onto block 412. If not, then the process moves back to block 404.

Figure 5:
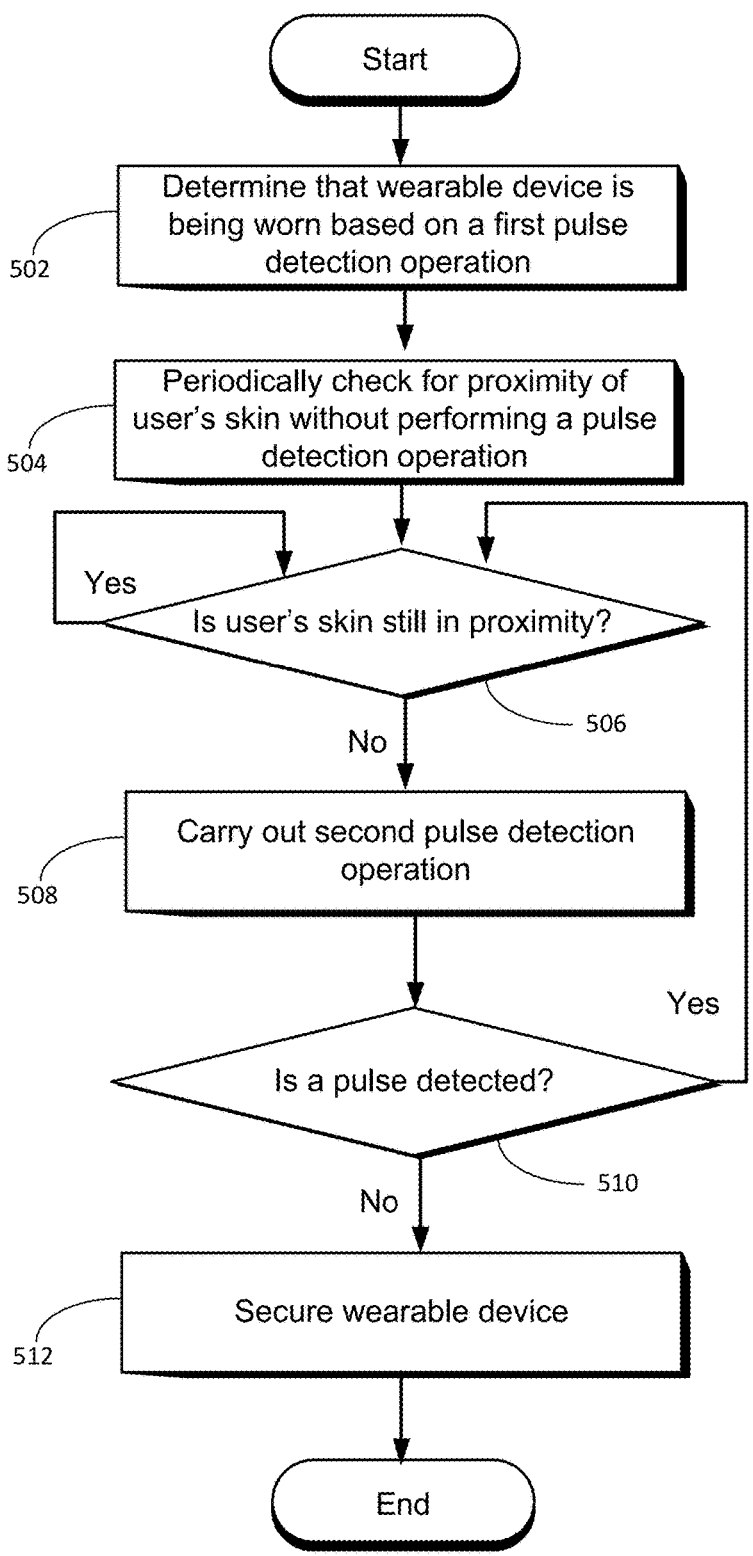

Turning to FIG. 5, operation of the wearable device 100 according to another embodiment is described. At block 502, the wearable device 100 determines that it is currently being worn based on a first pulse detection operation (e.g., by taking a PPG with the pulse sensor 104 and analyzing the results with the processor 202). At block 504, the wearable device periodically checks for the proximity of the user's skin (e.g., by conducting a proximity detection operation using the components of the pulse sensor 104). In an embodiment, checking for the proximity of the user's skin involves flashing the light source 214 at a power that is less than the power required for the pulse checking operations (e.g., flashing a green light-emitting diode at a lower intensity and for a shorter duration than would be required for taking a PPG). If the wearable device 100 determines that the user's skin is not proximal then, at block 508, the wearable device 100 carries out a second pulse detection operation. If, at block 510, the wearable device 100 detects a pulse in the second pulse detection operation, then the process moves back to block 506. If, on the other hand, the wearable device does not detect a pulse in the second pulse detection operation, the process moves to block 512, at which the wearable device 100 secures itself.

Figure 6:
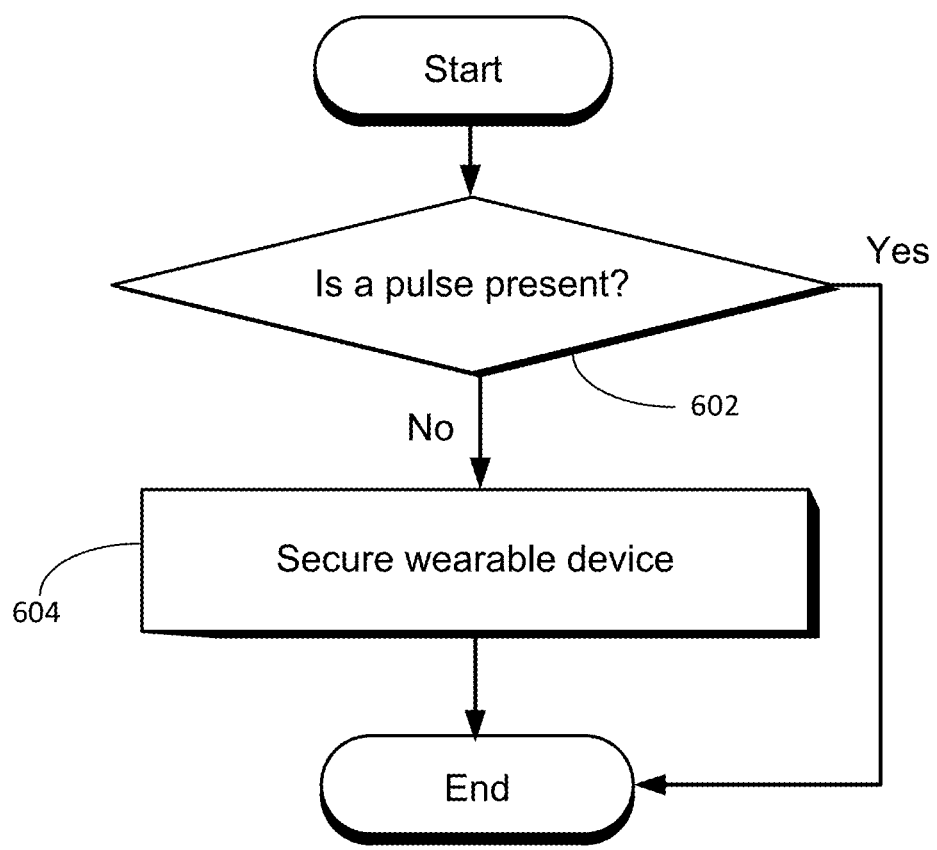

Turning to FIG. 6, operation of the wearable device 100 according to still another embodiment is described. In this embodiment, the wearable device 100 uses pulse detection, but does not necessarily use presence detection. At block 602, the wearable device 100 determines whether a pulse is present (e.g., by taking a PPG with the pulse sensor 104 and analyzing the results with the processor 202). If the wearable device 100 determines that a pulse is present, then the procedure ends. If the wearable device determines that a pulse is not present, the wearable device secures itself at block 604.

While one or more embodiments of the have been described with reference to the figures, it will be understood by those of ordinary skill in the art that various changes in form and details may be made therein without departing from their spirit and scope of as defined by the following claims.

What is claimed is:

1. A method comprising:
   responsive to determining a first motion of a wearable electronic device that is associated with a user, determining whether a pulse of the user is present, wherein determining whether the pulse of the user is present comprises analyzing a photoplethysmogram;
   responsive to determining that the pulse of the user is not present, securing the wearable electronic device, wherein securing the wearable electronic device comprises locking a user interface of the wearable electronic device and transmitting a signal to a paired companion device indicating that the wearable electronic device is not being worn; and
   responsive to determining a second motion of the wearable electronic device and determining that the pulse of the user is present:
      obtaining a baseline reflection profile of reflected light from the user's skin;
      setting, based on the baseline reflection profile, an upper threshold value and a lower threshold value that are associated with a wavelength or a frequency of detected light;
      responsive to determining that the wavelength or the frequency of detected light that is reflected from the user's skin fails to be between the upper threshold value and the lower threshold value, determining that the user's skin is not proximal to the wearable electronic device; and
      responsive to determining that the user's skin is not proximal to the wearable electronic device, repeating the determining of whether the pulse of the user is present.

2. A method comprising:
   determining, based on a performance of a first pulse detection operation, that a wearable electronic device is currently being worn by a user;
   responsive to determining that the wearable electronic device is currently being worn by the user, periodically checking for a proximity of the user's skin to the wearable electronic device without performing any pulse detection operation, wherein periodically checking for the proximity of the user's skin to the wearable electronic device comprises periodically flashing light at a power less than that used for a photoplethysmogram;
   determining, during the periodic checking, that the user's skin is not in the proximity to the wearable electronic device, wherein determining that the user's skin is not in the proximity to the wearable electronic device comprises:
      obtaining a baseline reflection profile of reflected light from the user's skin;
      setting, based on the baseline reflection profile, an upper threshold value and a lower threshold value that are associated with a wavelength or a frequency of detected light; and
      responsive to determining that the wavelength or the frequency of detected light that is reflected from the user's skin fails to be between the upper threshold value and the lower threshold value, determining that the user's skin is not in the proximity to the wearable electronic device; and
   responsive to determining that the user's skin is not in the proximity to the wearable electronic device:
      performing a second pulse detection operation; and
      responsive to determining that a pulse of the user is not detected during the second pulse detection operation, securing the wearable electronic device, wherein securing the wearable electronic device comprises locking a user interface of the wearable electronic device and transmitting a signal to a paired companion device indicating that the wearable electronic device is not being worn.

3. A wearable electronic device, comprising:
   a photo sensor configured to generate signals based on detected light; and
   a processor configured to:
      responsive to determining a first motion of a wearable electronic device that is associated with a user, determine whether a pulse of the user is present, wherein determining whether the pulse of the user is present comprises analyzing a photoplethysmogram;
      responsive to determining that the pulse of the user is not present, secure the wearable electronic device at least by locking a user interface of the wearable electronic device and transmitting a signal to a paired companion device indicating that the wearable electronic device is not being worn; and
      responsive to determining a second motion of the wearable electronic device and determining that the pulse of the user is present:
         obtain a baseline reflection profile of reflected light from the user's skin;
         set, based on the baseline reflection profile, an upper threshold value and a lower threshold value that are associated with a wavelength or a frequency of detected light;
         responsive to determining that the wavelength or the frequency of detected light that is reflected from the user's skin fails to be between the upper threshold value and the lower threshold value, determine that the user's skin is not proximal to the wearable electronic device; and
         responsive to determining that the user's skin is not proximal to the wearable electronic device, repeat the determining of whether the pulse of the user is present.

4. The wearable electronic device of claim 3, further comprising a light source that shines light in a direction, such that when the electronic device is worn by the user, the light reflects off of the user and is sensed by the photo sensor.

5. The wearable electronic device of claim 4, wherein the processor is further configured to determine whether the pulse of the user is present at least by:
   acquiring the photoplethysmogram using the light source and the photo sensor.

6. A wearable electronic device, comprising:
a light source;
a photo sensor configured to generate signals based on sensed light from the light source; and
a processor configured to:
determine, based on a performance of a first pulse detection operation, that the wearable electronic device is currently being worn by a user;
responsive to determining that the wearable electronic device is currently being worn by the user, periodically check for a proximity of the user's skin to the wearable electronic device without performing any pulse detection operation, wherein the processor is configured to periodically check for the proximity of the user's skin to the wearable electronic device at least by a periodically flashing light from the light source at a power less than that used for a photoplethysmogram;
determine, during the periodic checking, that the user's skin is not in the proximity to the wearable electronic device, wherein the processor is configured to determine that the user's skin is not in the proximity to the wearable electronic device at least by being configured to:
  obtain a baseline reflection profile of reflected light from the user's skin;
  set, based on the baseline reflection profile, an upper threshold value and a lower threshold value that are associated with a wavelength or a frequency of detected light; and
  responsive to determining that the wavelength or the frequency of detected light that is reflected from the user's skin fails to be between the upper threshold value and the lower threshold value, determine that the user's skin is not in the proximity to the wearable electronic device; and
responsive to determining that the user's skin is not in the proximity to the wearable electronic device:
  perform a second pulse detection operation; and
  responsive to determining that a pulse of the user is not detected during the second pulse detection operation, secure the wearable electronic device at least by locking a user interface of the wearable electronic device and transmitting a signal to a paired companion device indicating that the wearable electronic device is not being worn.

7. The method of claim 1, further comprising:
acquiring the photoplethysmogram using a light source and a photo sensor of the wearable electronic device.

8. The method of claim 2, further comprising:
acquiring the photoplethysmogram for at least one of the first pulse detection operation or the second pulse detection operation using a light source and a photo sensor of the wearable electronic device.

\* \* \* \* \*